United States Patent
Timken et al.

(10) Patent No.: US 8,987,159 B2
(45) Date of Patent: Mar. 24, 2015

(54) INTEGRATED ALKYLATION PROCESS TO MAKE BLENDED ALKYLATE GASOLINE

(71) Applicants: Hye Kyung Cho Timken, Albany, CA (US); Izadyar Dalvand, Richmond, CA (US); Douglas Robert Cyr, Livermore, CA (US); Michael Tung-hai Cheng, Berkeley, CA (US); Huping Luo, Richmond, CA (US); Shawn Shlomo Winter, Salt Lake City, UT (US); Michael Sean Driver, San Francisco, CA (US); Donald Henry Mohr, Orinda, CA (US)

(72) Inventors: Hye Kyung Cho Timken, Albany, CA (US); Izadyar Dalvand, Richmond, CA (US); Douglas Robert Cyr, Livermore, CA (US); Michael Tung-hai Cheng, Berkeley, CA (US); Huping Luo, Richmond, CA (US); Shawn Shlomo Winter, Salt Lake City, UT (US); Michael Sean Driver, San Francisco, CA (US); Donald Henry Mohr, Orinda, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/193,810

(22) Filed: Feb. 28, 2014

(65) Prior Publication Data
US 2014/0179977 A1    Jun. 26, 2014

Related U.S. Application Data

(62) Division of application No. 13/563,415, filed on Jul. 31, 2012, now Pat. No. 8,704,018.

(51) Int. Cl.
*B01J 38/48* (2006.01)
*C07C 2/54* (2006.01)
*G01N 33/22* (2006.01)
*C10L 1/06* (2006.01)
*C10L 1/16* (2006.01)
*B01J 38/10* (2006.01)
*C07C 9/16* (2006.01)
*C07C 13/16* (2006.01)
*C07C 13/18* (2006.01)
*B01J 38/00* (2006.01)
*B01J 31/02* (2006.01)

(52) U.S. Cl.
CPC ............. *G01N 33/225* (2013.01); *C10L 1/06* (2013.01); *C10L 1/1691* (2013.01); *B01J 38/10* (2013.01); *B01J 31/0277* (2013.01); *C10G 2300/301* (2013.01)
USPC .......................................................... 502/22

(58) Field of Classification Search
CPC ............ B01J 38/00; B01J 38/48; B01J 38/64; C07C 2/54; C07C 2/56; C07C 2/64; C07C 2/66; C07C 2/72; C07C 9/16; C07C 13/16; C07C 13/18
See application file for complete search history.

(56) References Cited

U.S. PATENT DOCUMENTS

| | | | |
|---|---|---|---|
| 5,421,167 A | 6/1995 | Verma et al. | |
| 6,395,945 B1 | 5/2002 | Randolph | |
| 7,432,408 B2 | 10/2008 | Timken et al. | |
| 7,432,409 B2 | 10/2008 | Elomari et al. | |
| 7,540,888 B2 | 6/2009 | Ryder et al. | |

(Continued)

*Primary Examiner* — Brian McCaig
(74) *Attorney, Agent, or Firm* — Susan M. Abernathy (57) ABSTRACT

We provide an extracted conjunct polymer naphtha (45), comprising a hydrogenated conjunct polymer naphtha, from a used ionic liquid catalyst, having a final boiling point less than 246° C. (475° F.), a Bromine Number of 5 or less, and at least 30 wt % naphthenes. We also provide a blended alkylate gasoline (97) comprising the extracted conjunct polymer naphtha (45), and integrated alkylation processes to make the extracted conjunct polymer naphtha (45) and the blended alkylate gasoline (97). We also provide a method to analyze alkylate products, by determining an amount of methylcyclohexane in the alkylate products (80).

11 Claims, 2 Drawing Sheets

(56) References Cited

U.S. PATENT DOCUMENTS

| | | |
|---|---|---|
| 7,553,999 B2 | 6/2009 | Elomari et al. |
| 7,569,740 B2 | 8/2009 | Elomari |
| 7,576,252 B2 | 8/2009 | Elomari et al. |
| 7,651,970 B2 | 1/2010 | Elomari et al. |
| 7,678,727 B2 | 3/2010 | Harris et al. |
| 7,691,771 B2 | 4/2010 | Harris et al. |
| 7,732,363 B2 | 6/2010 | Elomari et al. |
| 7,732,651 B2 | 6/2010 | Driver et al. |
| 7,825,055 B2 | 11/2010 | Elomari et al. |
| 7,919,664 B2 | 4/2011 | Hommeltoft et al. |
| 7,923,593 B2 | 4/2011 | Hommeltoft et al. |
| 7,923,594 B2 | 4/2011 | Hommeltoft |
| 7,955,495 B2 | 6/2011 | Hommeltoft et al. |
| 8,101,809 B2 | 1/2012 | Elomari et al. |
| 8,124,821 B2 | 2/2012 | Elomari et al. |
| 8,202,413 B2 | 6/2012 | Joensen et al. |
| 8,388,828 B2 | 3/2013 | Elomari et al. |
| 8,487,154 B2 | 7/2013 | Timken et al. |
| 2007/0249486 A1* | 10/2007 | Elomari et al. ............... 502/53 |
| 2009/0242840 A1 | 10/2009 | Olschimke et al. |
| 2010/0147740 A1 | 6/2010 | Elomari et al. |
| 2010/0270205 A1 | 10/2010 | Lopez et al. |
| 2012/0024750 A1 | 2/2012 | Zhan et al. |
| 2013/0066130 A1 | 3/2013 | Luo et al. |
| 2013/0066132 A1 | 3/2013 | Cleverdon et al. |
| 2013/0066133 A1 | 3/2013 | Cleverdon et al. |

\* cited by examiner

INTEGRATED ALKYLATION PROCESS TO MAKE BLENDED ALKYLATE GASOLINE

This application is a divisional of U.S. application Ser. No. 13/563,415, now U.S. Pat. No. 8,704,018, filed Jul. 31, 2012, and herein incorporated in its entirety. U.S. application Ser. No. 13/563,415 was assigned to Art Unit 1771.

This application is a continuation of: "ALKYLATION PROCESS WITH RECYCLE OF HYDROGEN AND RECOVERY OF HYDROGEN CHLORIDE", with the U.S. application Ser. No. 13/563,355, filed Jul. 31, 2012; and "HYDROGEN RECYCLE AND HYDROGEN CHLORIDE RECOVERY IN AN ALKYLATION PROCESS", with the U.S. application Ser. No. 13/563,385, filed Jul. 31, 2012; both herein incorporated in their entireties.

TECHNICAL FIELD

This application is directed to compositions of extracted conjunct polymer naphtha and blended alkylate gasoline; and processes for their production.

BACKGROUND

High-quality alkylate gasolines are needed for spark-ignited automotive engines. It is desired that new or more efficient processes be developed to produce these gasolines, and that these gasolines have improved qualities.

SUMMARY

This application provides an extracted conjunct polymer naphtha (45), comprising a hydrogenated conjunct polymer, from a used ionic liquid catalyst, having a final boiling point less than 246° C. (475° F.), a Bromine Number of 5 or less, and at least 30 wt % naphthenes.

This application provides a blended alkylate gasoline (97), comprising an extracted conjunct polymer naphtha (45) and alkylate products (80), wherein the extracted conjunct polymer naphtha (45) has a final boiling point less than 246° C. (475° F.), a Bromine Number of 5 or less, and at least 30 wt % naphthenes.

This application provides an extracted conjunct polymer naphtha (45), made by a process comprising:
  a. regenerating a used ionic liquid catalyst comprising a conjunct polymer in a hydrogenation reactor (100) to make a regenerated catalyst effluent (10);
  b. mixing the regenerated catalyst effluent (10) or a separated liquid from the regenerated catalyst effluent (10) with a conjunct polymer extraction solvent (55); and
  c. separating out the conjunct polymer extraction solvent (55) to produce the extracted conjunct polymer naphtha (45); wherein the extracted conjunct polymer naphtha (45) has a final boiling point less than 246° C. (475° F.), a Bromine Number of 5 or less, and at least 30 wt % naphthenes.

This application also provides a blended alkylate gasoline (97), made by a process comprising:
  a. regenerating a used ionic liquid catalyst comprising a conjunct polymer in a hydrogenation reactor (100) to make a regenerated catalyst effluent (10);
  b. mixing the regenerated catalyst effluent (10) or a separated liquid from the regenerated catalyst effluent (10) with an effluent from an alkylation reactor (40); and
  c. separating out an ionic liquid catalyst stream (60) from the mixture made in step b) to produce the blended alkylate gasoline (97) comprising greater than 50 wppm methylcyclohexane.

This application also provides an integrated alkylation process, comprising:
  a. regenerating a used ionic liquid catalyst comprising a conjunct polymer in a hydrogenation reactor (100) to make a regenerated catalyst effluent (10);
  b. mixing the regenerated catalyst effluent (10) or a separated liquid from the regenerated catalyst effluent (10) with an effluent from an alkylation reactor (40); and
  c. separating out an ionic liquid catalyst stream (60) from the mixture made in step b) to produce a blended alkylate gasoline (97) comprising greater than 50 wppm methylcyclohexane.

This application also provides a method to analyze alkylate products, comprising: determining an amount of methylcyclohexane in alkylate products (80) and based on the amount, estimating a quantity of extracted conjunct polymer naphtha (45) in the alkylate products (80).

DETAILED DESCRIPTION

Figure 1:
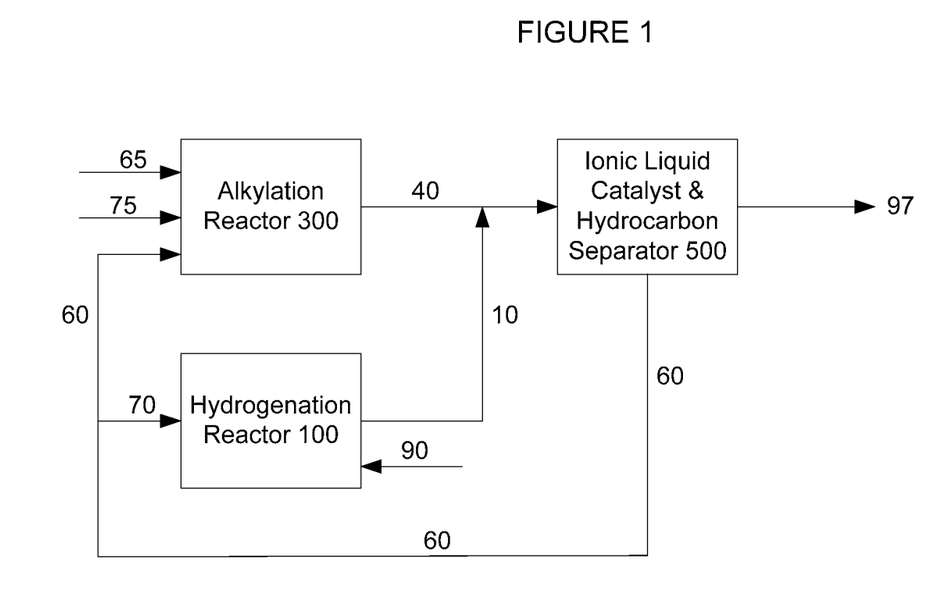
FIG. 1 is a diagram of an integrated alkylation process, demonstrating direct blending of extracted conjunct polymer naphtha with alkylate products.

Referring to FIG. 1, isoparaffin feed (65) and olefin feed (75) are fed to an alkylation reactor (300). The effluent from an alkylation reactor (40) is blended with regenerated catalyst effluent (10) and fed to an ionic liquid catalyst and hydrocarbon separator (500). The ionic liquid catalyst and hydrocarbon separator (500) separates the combined effluent from an alkylation reactor (40) and from the regeneration unit (10) into blended alkylate gasoline (97) and an ionic liquid catalyst stream (60). The ionic liquid catalyst stream (60) is recycled to the alkylation reactor (300). A portion of the ionic liquid catalyst stream (60) is used catalyst (70) that is fed to a hydrogenation reactor (100) for regeneration. Hydrogen (90) is also fed to the hydrogenation reactor. The regenerated catalyst effluent (10) is produced in the hydrogenation reactor (100) and blended with the effluent from an alkylation reactor (40) as described above. The blended alkylate gasoline (97) comprises alkylate products (80) produced in the alkylation reactor (300) as well as extracted conjunct polymer naphtha (45).

Figure 2:
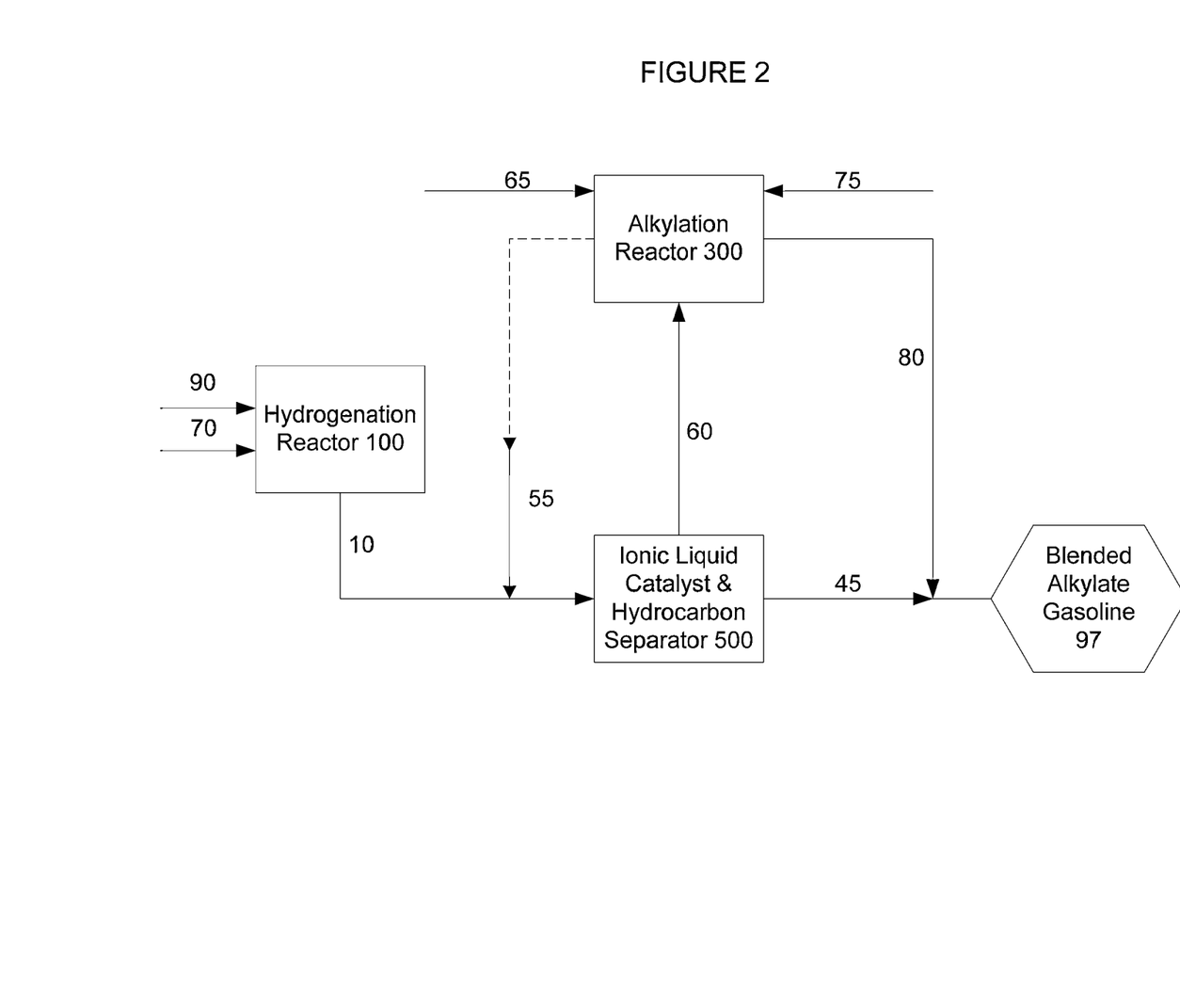
FIG. 2 is a diagram of an integrated alkylation process to produce extracted conjunct polymer naphtha.

Referring to FIG. 2, hydrogen (90) and used catalyst (70) (e.g., used ionic liquid catalyst) are fed to a hydrogenation reactor (100). The hydrogenation reactor (100) produces a regenerated catalyst effluent (10) that is mixed with a conjunct polymer extraction solvent (55) and the mixture is fed to an ionic liquid catalyst and hydrocarbon separator (500). The ionic liquid catalyst and hydrocarbon separator (500) separates the mixture of hydrogenation reactor effluent and the extraction solvent into an ionic liquid catalyst stream (60) and extracted conjunct polymer naphtha (45). The ionic liquid catalyst stream (60) from the ionic liquid catalyst and hydrocarbon separator (500), isoparaffin feed (65) and olefin feed (75) are fed to an alkylation reactor (300). In one embodiment, the conjunct polymer extraction solvent (55) is at least partially an effluent from the alkylation reactor (300). Alkylate products (80) are produced by the alkylation reactor (300). The extracted conjunct polymer naphtha (45) is blended with the alkylate products (80) produced by the alkylation reactor (300) to make blended alkylate gasoline (97).

Extracted Conjunct Polymer Naphtha (45)

The extracted conjunct polymer naphtha (45) has a composition that makes it suitable for blending into alkylate products (80) to make high quality alkylate gasoline. The extracted conjunct polymer naphtha (45) has at least 30 wt % naphthenes. For example, it can have at least 40 wt %, or at least 50 wt % naphthenes. In one embodiment, the extracted conjunct polymer naphtha (45) can have at least 30 wt % up to 90 wt % naphthenes. In one embodiment, the extracted conjunct polymer naphtha (45) has at least 40 wt %, at least 50 wt %, at least 60 wt %, or at least 70 wt % naphthenes and isoparaffins. In one embodiment, the extracted conjunct polymer naphtha (45) has from at least 40 wt % to 95 wt % naphthenes and isoparaffins. In one embodiment, the extracted conjunct polymer naphtha (45) has at least 10 wt % isoparaffins, such as from at least 10 wt % to 40 wt % isoparaffins.

In one embodiment, the extracted conjunct polymer naphtha (45) has at least 60 wt % carbon numbers in the range of C5 through C10. The extracted conjunct polymer naphtha (45) can have up to 99 wt % carbon numbers in the range of C5 through C10.

The extracted conjunct polymer naphtha (45) has a low Bromine Number of 5 or less. In other embodiments, the Bromine Number can be from <1 to 5, or 3 or less. In one embodiment, the low Bromine Number is achieved without any post-processing of the regenerated catalyst effluent (10) other than separating, such as can be performed in the ionic liquid catalyst and hydrocarbon separator (500).

The extracted conjunct polymer naphtha (45) has a high octane number. In one embodiment, the extracted conjunct polymer naphtha (45) has a RON of 60 or greater, 70 or greater, up to 90.

The extracted conjunct polymer naphtha (45) has a final boiling point that makes it useful for blending into alkylate gasoline. The extracted conjunct polymer naphtha (45) has a final boiling point less than 246° C. In one embodiment the extracted conjunct polymer naphtha (45) has a boiling point range distribution from 32° C. to 245° C.

In one embodiment, the extracted conjunct polymer naphtha (45) is from a used catalyst (70) that is an ionic liquid catalyst. The ionic liquid catalyst can be the same ionic liquid catalyst that was used to produce the alkylate products (80) which can be blended with the extracted conjunct polymer naphtha (45) to make the blended alkylate gasoline (97).

In one embodiment the extracted conjunct polymer naphtha (45) comprises at least 3 wt % up to 30 wt % methylcyclohexane. The content of naphthenes, isoparaffins and methylcyclohexane are measured by detailed hydrocarbon analysis by gas chromatography such as a method defined in ASTM6729 test.

Blended Alkylate Gasoline (97)

The blended alkylate gasoline (97) comprises extracted conjunct polymer naphtha (45) and alkylate products (80).

In one embodiment, the blended alkylate gasoline (97) comprises the extracted conjunct polymer naphtha (45) having the useful final boiling point and boiling point range, low bromine number, and high wt % naphthenes as described above. In one embodiment, the blended alkylate gasoline (97) comprises greater than 40 wt %, or greater than 50 wt %, and up to 95 wt % $C_7$ and $C_8$ hydrocarbons.

In one embodiment, the blended alkylate gasoline (97) comprises a high amount of trimethyl isomers in C8 hydrocarbons. For example, the blended alkylate gasoline (97) can comprise greater than 50 wt %, greater than 60 wt %, or greater than 70 wt %, up to 95 wt % trimethylpentane relative to the total C8 hydrocarbons.

In one embodiment, the blended alkylate gasoline (97) comprises C9 hydrocarbons that are mainly trimethyl isomers, such as from 50 wt % to 95 wt % trimethylhexane relative to the total C9 hydrocarbons. In one embodiment, the blended alkylate gasoline (97) comprises greater than 40 wt % up to 70 wt % of C8 hydrocarbons as 2,2,4-Trimethylpentane. In one embodiment, the blended alkylate gasoline (97) comprises a wt % of a total trimethylpentane that is 2,2,4-Trimethylpentane greater than 50 wt % up to 70 wt %.

In one embodiment, the blended alkylate gasoline (97) comprises at least 0.01 wt % of the extracted conjunct polymer naphtha (45). For example, the blended alkylate gasoline (97) can comprise from 0.01 wt % to 20.00 wt %, or 0.01 wt % to 5.00 wt %, extracted conjunct polymer naphtha (45).

In one embodiment, the blended alkylate gasoline (97) comprises measurable amounts of methylcyclohexane. For example, the blended alkylate gasoline (97) can have from greater than 50 wppm to 500 wppm methylcyclohexane. In one embodiment, the blended alkylate gasoline (97) comprises greater than 50 wppm methylcyclohexane.

In one embodiment, the blended alkylate gasoline (97) meets the requirements of automotive fuels for ground vehicles equipped with spark-ignition engines, as defined in ASTM D4814-11b. For example, the blended alkylate gasoline (97) can have a solvent washed gum less than 5.0 mg/100 mL. The blended alkylate gasoline (97) can have either a slight tarnish or no tarnish in a silver strip test, as defined in ASTM D4814-11b. Additionally, the blended alkylate gasoline (97) can have a slight tarnish (rating of 1a or 1b) in a copper strip test, as defined in ASTM D130-10. A 1a copper strip test result means that the copper strip at the end of the test is light orange, almost the same as the freshly prepared copper strip. It is not possible to have a copper strip test result better than 1a, as even a completely noncorrosive sample will discolor the copper strip to light orange.

In one embodiment, the blended alkylate gasoline (97) has excellent road octane performance in vehicles with spark-ignition engines. For example, the antiknock index (AKI), as defined in ASTM D4814-11b, can be from 87 to 95. In one embodiment, the blended alkylate gasoline (97) has a RON greater than 85.

Ionic Liquid Catalyst

The ionic liquid catalyst is an organic salt or mixture of salts. The ionic liquid catalyst can be characterized by the general formula Q+A−, wherein Q+ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$—, alkyl-aryl sulfonate, and benzene sulfonate (e.g., 3-sulfurtrioxyphenyl). In one embodiment the ionic liquid catalyst is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl-substituted-pyridinium halide compounds for example 1-butylpyridinium halide, benzylpyridinium halide, or hydrocarbyl-substituted-imidazolium halides, such as for example, 1-ethyl-3-methyl-imidazolium chloride.

In one embodiment, the ionic liquid catalyst is an organic salt that is hygroscopic in nature and has a tendency to attract and hold water molecules from the surrounding environment. With these ionic liquid catalysts, in order to maintain the integrity of the ionic liquid catalyst and its catalytic performance, the organic salts from which the ionic liquid catalyst is synthesized, are thoroughly dried before the catalyst synthesis, and moisture-free conditions are maintained during the alkylation reaction.

In one embodiment the ionic liquid catalyst is selected from the group consisting of hydrocarbyl-substituted-pyridinium chloroaluminate, hydrocarbyl-substituted-imidazolium chloroaluminate, quaternary amine chloroaluminate, trialkyl amine hydrogen chloride chloroaluminate, alkyl pyridine hydrogen chloride chloroaluminate, and mixtures thereof. For example, the used ionic liquid catalyst can be an acidic haloaluminate ionic liquid, such as an alkyl substituted pyridinium chloroaluminate or an alkyl substituted imidazolium chloroaluminate of the general formulas A and B, respectively.

In the formulas A and B; R, $R_1$, $R_2$, and $R_3$ are H, methyl, ethyl, propyl, butyl, pentyl or hexyl group, X is a chloroaluminate. In another embodiment, R, $R_1$, $R_2$, and $R_3$ are methyl, ethyl, propyl, butyl, pentyl or hexyl group, and X is a chloroaluminate. In one embodiment the X is $AlCl_4^-$, $Al_2Cl_7^-$, or $Al_3Cl_{10}^-$. In the formulas A and B, R, $R_1$, $R_2$, and $R_3$ may or may not be the same. In one embodiment the ionic liquid catalyst is N-butylpyridinium heptachlorodialuminate $[Al_2Cl_7^-]$. In one embodiment the ionic liquid catalyst is 1-Ethyl-3-methylimidazolium tetrachloroaluminate [emim$^+$][$AlCl_4$].

Alkylation Process to Make Extracted Conjunct Polymer Naphtha

The extracted conjunct polymer naphtha (45) can be made by an alkylation process comprising regenerating a used catalyst comprising a conjunct polymer. The alkylation process comprises regenerating a used ionic liquid catalyst comprising a conjunct polymer in a hydrogenation reactor (100) to make a regenerated catalyst effluent (10). In one embodiment, the used ionic liquid catalyst has been used in an alkylation reactor (300).

The used ionic liquid catalyst is regenerated in the hydrogenation reactor (100). In one embodiment, the hydrogenation reactor (100) contacts the used catalyst (70) with hydrogen (90) and a hydrogenation catalyst to regenerate the ionic liquid catalyst. In one embodiment, zeolites or molecular sieves are added to the hydrogenation catalyst to improve the catalyst's performance. In one embodiment, the hydrogenation catalyst is supported. Typical support materials for the hydrogenation catalyst are kieselguhr, alumina, silica, and silica-alumina. Other support materials include alumina-boria, silica-alumina-magnesia, silica-alumina-titania and materials obtained by adding zeolites and other complex oxides thereto. When used, the support material has adequate mechanical strength and chemical stability at the hydrogenation reaction temperature.

In one embodiment, the hydrogenation is carried out in the presence of a catalyst which usually comprises a metal or non metal hydrogenation component on a porous support material, such as a natural clay or a synthetic oxide. Examples of metal hydrogenation components that can be used are Fe, Co, Ni, Ru, Rh, Pd, Pt, Ir, Os, Cr, Mn, Ti, V, Zr, Mo, W, and mixtures thereof. Examples of non metal hydrogenation components are Te, As, and mixtures thereof. The hydrogenation components can be used singly or in combination.

The hydrogenation can be carried out over a broad range of hydrogen pressures, typically from about 50 to 3,000 psig. Hydrogenation conditions can include temperatures of −20° C. to 400° C., or 50° C. to 300° C.; and total pressures of atmospheric to 5,000 psig, or 50 to 2,500 psig. Hydrogenation contact times can be from 0.1 minute to 24 hours, such as 10 minutes to 12 hours. Feed to catalyst ratios during the hydrogenation can vary from 0.1 to 10 vol/vol/hour. A normal hydrocarbon can optionally be used as a solvent in the hydrogenation reactor (100).

Examples of hydrogenation of ionic liquid catalysts for regeneration, for example, are given in U.S. Pat. No. 7,691,771, U.S. Pat. No. 7,651,970, U.S. Pat. No. 7,678,727, and U.S. Pat. No. 7,825,055. In one embodiment, conditions in the hydrogenation reactor (100) are selected to produce a hydrogenated conjunct polymer having a final boiling point less than 246° C. (475° F.). In another embodiment, conditions in the hydrogenation reactor (100) are selected to produce a hydrogenated conjunct polymer having a property selected from the group of a final boiling point less than 246° C. (475° F.), a Bromine Number of 5 or less, at least 30 wt % naphthenes, at least 3 wt % methylcyclohexane, and combinations thereof.

The alkylation process additionally comprises mixing the regenerated catalyst effluent (10) or a separated liquid from the regenerated catalyst effluent (10) with a conjunct polymer extraction solvent (55). The conjunct polymer extraction solvent (55) can be any hydrocarbon that can serve as a solvent or reactant for the alkylation process. Examples of suitable conjunct polymer extraction solvents for alkylation processes making alkylate gasoline are isobutane, n-butane, alkylate gasoline and mixtures thereof.

In one embodiment at least a portion of the conjunct polymer extraction solvent (55) comes from an effluent from an alkylation reactor (40). For example, the conjunct polymer extraction solvent (55) from an alkylation reactor (300) can comprise alkylate products, unreacted isoparaffins, n-butane, or mixtures thereof.

In one embodiment, at least a portion (up to the full amount) of the conjunct polymer extraction solvent (55) can come from an effluent from an alkylation reactor (40). For example, the conjunct polymer extraction solvent (55) can comprise from at least 25 wt % to 100 wt % of an effluent from an alkylation reactor (40). In one embodiment, up to 100 wt % of the conjunct polymer extraction solvent is an effluent from an alkylation reactor (40), or portion thereof.

In one embodiment, the alkylation process to make extracted conjunct polymer naphtha additionally comprises separating out the conjunct polymer extraction solvent (55) to produce the extracted conjunct polymer naphtha (45). In one embodiment, the separating is done in an ionic liquid catalyst and hydrocarbon separator (500). Examples of ionic liquid catalyst and hydrocarbon separators that can be used include centrifuges, liquid-liquid extractors or in-line mixers in combination with selective filters, settling tanks, and coalescers. Examples of suitable coalescers are described in U.S. Pat. No. 8,067,656.

Direct Blending to Make Blended Alkylate Gasoline (97)

Blended alkylate gasoline (97) can be made by direct blending of extracted conjunct polymer naphtha (45) with alkylate products (80) without an extraction step to remove the extracted conjunct polymer naphtha (45) prior to blending. The blending can occur prior to the separation step in the ionic liquid catalyst and hydrocarbon separator (500). This embodiment is shown in FIG. 1. In one embodiment, an integrated alkylation process is used to make the blended alkylate gasoline (97). The integrated alkylation process can comprise:

a. regenerating a used ionic liquid catalyst comprising a conjunct polymer in a hydrogenation reactor (100) to make a regenerated catalyst effluent (10);
   b. mixing the regenerated catalyst effluent (10) or a separated liquid from the regenerated catalyst effluent (10) with an effluent from an alkylation reactor (40); and
   c. separating out an ionic liquid catalyst stream (60) from the mixture made in step b) to produce a blended alkylate gasoline (97) comprising greater than 50 wppm methylcyclohexane.

In one embodiment the blended alkylate gasoline (97) made by the integrated alkylation process has properties as described previously.

In one embodiment the integrated alkylation process to make the blended alkylate gasoline (97) uses conditions in the hydrogenation reactor (100) that are selected to produce a hydrogenated conjunct polymer having a final boiling point less than 246° C. (475° F.), a Bromine Number of 5 or less, and at least 30 wt % naphthenes. In one embodiment, conditions in the hydrogenation reactor (100) are selected to produce a hydrogenated conjunct polymer having a final boiling point less than 246° C. (475° F.). In another embodiment, conditions in the hydrogenation reactor (100) are selected to produce a hydrogenated conjunct polymer having a property selected from the group of a final boiling point less than 246° C. (475° F.), a Bromine Number of 5 or less, at least 30 wt % naphthenes, at least 3 wt % methylcyclohexane, and combinations thereof.

EXAMPLES

Example 1

Ionic Liquid Catalyst Comprising Anhydrous Metal Halide

Various ionic liquid catalysts made of metal halides such as $AlCl_3$, $AlBr_3$, $GaCl_3$, $GaBr_3$, $InCl_3$, and $InBr_3$ could be used for the catalytic processes. N-butylpyridinium chloroaluminate ($C_5H_5NC_4H_9Al_2Cl_7$) ionic liquid catalyst is an example used in our process. The catalyst has the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Alkylation of $C_3/C_4$ Olefin and Isobutane to make Alkylate Gasoline

Refinery isobutane containing 85% isobutane and 15% n-butane was used for this study, after drying the refinery isobutane with 13x molecular sieve. A refinery olefin stream containing $C_3$ and $C_4$ olefins ($C_3/C_4$ Olefin) from a Fluid Catalytic Cracking Unit (FCC unit) was dried with 13x molecular sieve and isomerized with a $Pd/Al_2O_3$ catalyst at 150° F., and 250 psig in the presence of hydrogen to produce isomerized $C_4$ and $C_3$ olefin feed with the composition shown in Table 1.

TABLE 1

| Composition of Olefin Feed | |
|---|---|
| Composition | Mol % |
| Propane, C3 | 13.3 |
| Propylene, C3= | 25.4 |
| 1-Butene, 1-C4= | 2.3 |
| 2-Butene, 2-C4= | 16.2 |
| Isobutylene, i-C4= | 6.7 |
| n-Butane, nC4 | 12.4 |
| Isobutane, iC4 | 22.2 |
| C5+ | 1.6 |
| Sum | 100.0 |

Evaluation of $C_3/C_4$ olefins alkylation with isobutane was performed in a continuously stirred tank reactor. An 8:1 molar mixture of isobutane and olefin was fed to the reactor while vigorously stirring. An ionic liquid catalyst as described in Example 1 was fed to the reactor via a second inlet port targeted to occupy 6 vol % in the reactor. A small amount of n-butyl chloride was added to produce anhydrous HCl gas in situ. The average residence time in the reactor (combined volume of feeds and catalyst) was about 12 minutes. The outlet pressure was maintained at 200 psig and the reactor temperature was maintained at 95° F. (35° C.) using external cooling.

The reactor effluent was separated with a coalescing separator into a hydrocarbon phase and an ionic liquid catalyst phase. The hydrocarbon phase was further separated with three distillation columns into multiple streams, including: a gas stream containing $C_3^-$ fraction, an $nC_4$ stream, an $iC_4$ stream, and an alkylate stream. The ionic liquid catalyst was recycled back to the alkylation reactor (300) for repeated use. To maintain the activity of the ionic liquid catalyst, a fraction of used ionic liquid catalyst was sent to a hydrogenation reactor (100) for reduction of the conjunct polymer level in the ionic liquid catalyst. We maintained the conjunct polymer level of the ionic liquid catalyst at 2-6% level with the hydrogenation and also obtained good alkylate gasoline properties (see Table 3, $1^{st}$ column) The amount of conjunct polymer in the ionic liquid catalyst was determined using an FT-IR quantitation method described in U.S. patent application Ser. No. 13/108,607, filed on May 16, 2011.

Example 3

Regeneration of Ionic Liquid Catalyst and Production of Extracted Conjunct Polymer Naphtha (45)

Used ionic liquid catalyst containing 5 wt % conjunct polymer was regenerated by passing the ionic liquid catalyst through a hydrogenation reactor (100) under $H_2$ atmosphere (hydro-regeneration). Hydrogen (90) gas with 99+ wt % purity was used. The hydro-regeneration of ionic liquid catalyst was performed in a hydrogenation reactor (100) operated at 350° F. (177° C.), 350 psig, 5000 scf $H_2$/bbl ionic liquid catalyst, and 0.2 liquid hourly space velocity (LHSV) in the presence of a hydrogenation catalyst containing Pt and Pd.

The regenerated catalyst effluent (10) from the hydrogenation reactor (100) was separated in a separator (400) into gas and liquid streams. At these conditions, 80 wt % of the conjunct polymer in the ionic liquid catalyst was converted to a light hydrocarbon material having a final boiling point less than 475° F. (246° C.), and the regenerated ionic liquid catalyst contained less than 1% conjunct polymer. The offgas (50) from the separator (400) contained 95% H$_2$ and 6000 ppm of HCl. The offgas (50) also contained 5 vol % of C$_3$-C$_6$ light hydrocarbons, while the bulk of the light hydrocarbon material was propane and isobutane.

The regenerated ionic liquid catalyst was sent to an liquid-liquid extraction unit (an ionic liquid catalyst and hydrocarbon separator (500)) with conjunct polymer extraction solvent (55) that was isobutane. In the ionic liquid catalyst and hydrocarbon separator (500), the conjunct polymer naphtha was extracted from the ionic liquid catalyst into the isobutane phase. The isobutane and conjunct polymer naphtha mixture was sent to a stripper to remove isobutane, and then a pure stream of extracted conjunct polymer naphtha (45) was obtained. The regenerated ionic liquid catalyst, free of extractable conjunct polymer naphtha, was combined with used ionic liquid catalyst and sent to the alkylation reactor (300).

Example 4

Composition of Extracted Conjunct Polymer Naphtha (45)

The composition of the extracted conjunct polymer naphtha (45) from Example 3 was analyzed with detailed hydrocarbon analysis using gas chromatography (DHA GC) by a method derived from ASTM D6729 method. To improve identifications of GC species, we used 60 meter high resolution dual columns (one polar column and one non-polar column) With the GC in combination with GC-MS, nearly all of the alkylate peaks were assigned. Those peaks that were not identified were grouped in a "Not Classified" category. The break-downs of the carbon number and molecular class of the extracted conjunct polymer naphtha (45) are shown in Table 2.

The amount of methylcyclohexane in the product was determined by the detailed hydrocarbon analysis chromatography (DHA GC) method. This improved GC method derived from ASTM D6729 method has a 10 ppm detection limit. The conventional ASTM D6729 method with single 100 M non-polar column was also used to measure the methylcyclohexane content, and the results by these two methods were comparable. The conventional ASTM D6729 method has a 50 ppm detection limit.

TABLE 2

Composition of Extracted Conjunct Polymer Naphtha (45)
Carbon Number Distribution and Molecular Class

| Carbon Number | N-Paraffin | I-Paraffin | Olefin | Naphthene | Aromatic | Not Classified | Total Per Carbon |
|---|---|---|---|---|---|---|---|
| C4, wt % | 1.2 | 0.6 | 0.0 | 0 | **** | **** | 1.8 |
| C5, wt % | 0.6 | 3.9 | 0.0 | 1.7 | **** | **** | 6.2 |
| C6, wt % | 0.6 | 4.8 | 0.1 | 8.7 | 0 | **** | 14.1 |
| C7, wt % | 0.1 | 2.0 | 0.0 | 15.2 | 0 | **** | 17.3 |
| C8, wt % | 0.1 | 1.9 | 0.1 | 27.1 | 1.8 | 0 | 31.0 |
| C9, wt % | 0.1 | 6.7 | 0.0 | 10.6 | 1.6 | 1.7 | 20.6 |
| C10, wt % | 0.0 | 2.3 | 0.0 | 0.2 | 1.8 | 0.4 | 4.7 |
| C11, wt % | 0.1 | 0.4 | 0.0 | 0 | 0.4 | 0.4 | 1.3 |
| C12+, wt % | 0.0 | 1.1 | 0.0 | 0 | 0.3 | 1.3 | 2.8 |
| Total, wt % | 3.0 | 23.6 | 0.2 | 63.4 | 5.9 | 3.8 | 100.0 |

The results in Table 2 indicated that the extracted conjunct polymer naphtha (45) was fully saturated, gasoline-boiling-range material with the typical carbon numbers in the range of C$_5$ through C$_{10}$. The extracted conjunct polymer naphtha (45) contained significant amounts of naphthenes (63.4%) and isoparaffins (23.6%).

We found that methylcyclohexane (C$_7$) was the most abundant naphthene species in the extracted conjunct polymer naphtha. The extracted conjunct polymer naphtha contained 12.5 wt % of methylcyclohexane.

Example 5

Properties of Alkylate Products (80), Extracted Conjunct Polymer Naphtha (45) and a Blended Alkylate Gasoline (97)

Properties of the alkylate products (80) from Example 2 and extracted conjunct polymer naphtha (45) from Example 3 are summarized in Table 3. Also, a blend of 0.2 vol % extracted conjunct polymer naphtha (45) and 99.8% alkylate gasoline was prepared and its properties are also summarized in Table 3.

TABLE 3

Properties of Alkylate Gasoline, Extracted Conjunct Polymer Naphtha, and a Gasoline Blend Containing Alkylate and Extracted Conjunct Polymer Naphtha

|  | Alkylate Gasoline with Ionic Liquid Catalyst (80) [As-Produced] | 100% Extracted Conjunct Polymer Naphtha (45) [As-Produced] | Blended Alkylate Gasoline (97) with 0.2 vol % Extracted Conjunct Polymer Naphtha (45) |
|---|---|---|---|
| Boiling Range Distribution, ASTM D86-11b |  |  |  |
| IBP, ° F. | 108 | 114 | 108 |
| 10%, ° F. | 168 | 185 | 169 |
| 50%, ° F. | 213 | 241 | 213 |

TABLE 3-continued

Properties of Alkylate Gasoline, Extracted Conjunct Polymer Naphtha, and a Gasoline Blend Containing Alkylate and Extracted Conjunct Polymer Naphtha

|  | Alkylate Gasoline with Ionic Liquid Catalyst (80) [As-Produced] | 100% Extracted Conjunct Polymer Naphtha (45) [As-Produced] | Blended Alkylate Gasoline (97) with 0.2 vol % Extracted Conjunct Polymer Naphtha (45) |
|---|---|---|---|
| 90%, °F. | 281 | 297 | 283 |
| Final Boiling Point, °F. | 396 | 439 | 401 |
| Bromine Number, ASTM D1159-07 (2012) | <1 | 1 | <1 |
| Research Octane Number, ASTM D2611-11e1 (RON) | 89 | 74 | 89 |
| Motor Octane Number, ASTM D2700-11e1 (MON) | 86 | 70 | 85 |
| AKI, ASTM D4814-11b | 87.5 | 72 | 87 |
| Methylcyclohexane Content, Modified ASTM D6729 | 30 ppm | 12.5 wt % | 310 ppm |

The extracted conjunct polymer naphtha (45) had a final boiling point of 439° F. (226° C.) and a 90 vol % boiling point of 297° F. (147° C.), indicating it was in the gasoline boiling range. The extracted conjunct polymer naphtha (45) was fully saturated in the hydrogenation reactor as shown by the Bromine Number of only 1. The Octane Numbers of the extracted conjunct polymer naphtha (45) were slightly worse compared to pure alkylate gasoline, but the volume used in the blending was very small and did not affect the Octane Number (either RON or MON) significantly. The properties of the blended alkylate gasoline (97) containing 0.2 vol % extracted conjunct polymer naphtha (45) and alkylate gasoline showed little change from the pure alkylate gasoline, indicating that the extracted conjunct polymer naphtha (45) was successfully blended to make high quality alkylate gasoline.

We found that tracking of methylcyclohexane content provided a useful estimating tool for determining how much of the extracted conjunct polymer naphtha was blended into the alkylate. The alkylate from example 2 contained very low methylcyclohexane of 30 ppm. The blend of 99.8 vol % alkylate and 0.2 vol % extracted conjunct polymer naphtha yielded 310 ppm of measured methylcyclohexane content. The measured methylcyclohexane value was within 10% of the estimated methylcyclohexane content for the blend (around 290 ppm estimated). We were able to use the content of methylcyclohexane to estimate the amount of the extracted conjunct polymer naphtha blended into the final alkylate.

Example 6

Composition of Alkylate Gasoline with Extracted Naphtha Blending

The composition of the blended alkylate gasoline (97) having 0.2 vol % extracted conjunct polymer naphtha (45) from Example 4 was analyzed with detailed hydrocarbon analysis GC using high resolution dual columns for the carbon number distribution and molecular class. These results are summarized in Table 4.

TABLE 4

Composition of Blended Alkylate Gasoline (97) with Extracted Conjunct Polymer Naphtha (45) Carbon Number Distribution and Molecular Class

| Carbon Number | N-Paraffin | I-Paraffin | Olefin | Naphthene | Aromatic | Not Classified | Total Per Carbon |
|---|---|---|---|---|---|---|---|
| C4, wt % | 0.6 | 0.3 | 0.0 | **** | **** | **** | 0.8 |
| C5, wt % | 0.3 | 7.5 | 0.0 | 0.0 | **** | **** | 7.8 |
| C6, wt % | 0.0 | 6.4 | 0.0 | 0.0 | 0 | **** | 6.5 |
| C7, wt % | 0.0 | 24.9 | 0.0 | 0.0 | 0 | **** | 24.9 |
| C8, wt % | 0.0 | 41.3 | 0.0 | 0.2 | 0 | 0 | 41.5 |
| C9, wt % | 0.0 | 7.8 | 0.0 | 0.2 | 0.0 | 0.1 | 8.0 |
| C10, wt % | 0.1 | 3.1 | 0.0 | 0.2 | 0.1 | 0.7 | 4.1 |
| C11, wt % | 0.0 | 2.8 | 0.0 | 0.0 | 0.5 | 1.6 | 4.9 |
| C12+, wt % | 0.0 | 0.5 | 0.0 | 0.0 | 0.1 | 0.7 | 1.3 |
| Total, wt % | 1.0 | 94.6 | 0.0 | 0.7 | 0.6 | 3.1 | 100.0 |

The overall composition of blended alkylate gasoline (97) with the extracted conjunct polymer naphtha (45) exhibited molecules that were predominately $C_5$ through $C_{10}$ isoparaffins and the blended alkylate gasoline (97) contained little undesirable gasoline components such as olefins, aromatics and normal paraffins.

The carbon number distribution and molecular class of this blended alkylate gasoline (97) was similar to the other alkylate gasoline made by conventional alkylation processes such as $H_2SO_4$ or HF alkylation. However, we found that there were differences in the $C_7$, $C_8$ and $C_9$ isoparaffin isomers in the blended alkylate gasoline (97), depending on the alkylation process of choice. Further analysis of the isoparaffin composition of the blended alkylate gasoline (97) with extracted conjunct polymer naphtha (45) is shown in Table 5.

TABLE 5

Composition of Blended Alkylate Gasoline with Extracted Conjunct Polymer Naphtha (45) Isoparaffin Isomer Distribution

| Alky Product Composition, wt % | | Alkylate & Extracted Naphtha Blend |
|---|---|---|
| Total C4 | 0.8 | 0.8 |
| Total C5 | 7.8 | 7.8 |
| 2,3-Dimethylbutane | 4.3 | |
| C6 Other | 2.1 | |
| Total C6 | | 6.5 |
| 2,3-Dimethylpentane | 11.9 | |
| 2,4-Dimethylpentane | 12.1 | |
| 223-Trimethylbutane | 0.1 | |
| C7 Other | 0.7 | |
| Total C7 | | 24.9 |
| 223-Trimethylpentane | 1.5 | |
| 224-Trimethylpentane | 20.1 | |
| 233-Trimethylpentane | 5.3 | |
| 234-Trimethylpentane | 5.5 | |
| Dimethylhexanes | 8.1 | |
| C8 Other | 1.0 | |
| Total C8 | | 41.5 |
| 225-Trimethylhexane | 5.4 | |
| 235-Trimethylhexane | 0.8 | |
| 244-Trimethylhexane | 0.2 | |
| 223-Trimethylhexane | 0.0 | |
| 224-Trimethylhexane | 0.1 | |
| C9 Other | 1.6 | |
| Total C9 | | 8.0 |
| Total C10-C11 | 9.0 | 9.0 |
| Total C12+ | 1.3 | 1.3 |
| sum | 100.0 | 100.0 |
| % 224-TMP/total TMP | 62 | |
| % Trimethylpentane/total C8 | 78 | |
| % Trimethylhexane/total C9 | 81 | |

The composition of the blended alkylate gasoline (97) had high selectivity for $C_7$ and $C_8$ isoparaffins via direct alkylation of $C_3$ and $C_4$ olefins with isobutane. The total $C_7$ and $C_8$ yield is 66.4%. The $C_8$ and $C_9$ hydrocarbon species were mainly trimethyl isomers (78.6 wt %), which are desirable since these molecules exhibit very high Octane Numbers. The percentage of trimethylpentane in total $C_8$ was 78 wt % and the percentage of trimethylhexane in total $C_9$ was 81 wt %. Among the trimethylpentane isomers, 2,2,4-Trimethylpentane was the most common isomer. The percentage of 2,2,4-Trimethylpentane relative to the total $C_8$ trimethylpentane isomers was 62%. This value of 2,2,4-Trimethylpentane relative to the total $C_8$ trimethylpentane was much higher than that of alkylate produced by sulfuric acid alkylation processes. Sulfuric acid alkylation processes generally produce alkylate with about 50 wt % or less of 2,2,4-Trimethylpentane or less compared to the total $C_8$.

Example 7

Process Simplification by Direct Blending of Extracted Conjunct Polymer Naphtha (45) with Alkylate Products (80)

The hydro-regeneration process for used ionic liquid catalyst can be simplified significantly by blending of extracted conjunct polymer naphtha (45) directly to the alkylate products (80). Example 3 above showed several steps required to recover a stream of extracted conjunct polymer naphtha (45). When we operated the hydro-regeneration conditions in the hydrogenation reactor (100) to produce a gasoline boiling range conjunct polymer naphtha at all times, then we did not need to isolate the extracted conjunct polymer naphtha (45). A much simpler, direct blending of extracted conjunct polymer naphtha (45) to alkylate was accomplished as follows.

Referring to FIG. 1, used catalyst (70) that was a used ionic liquid catalyst containing 5 wt % conjunct polymer was hydro-regenerated by passing the ionic liquid catalyst through a hydrogenation reactor (100) under $H_2$ atmosphere. Hydrogen (90) gas with 99+ wt % purity was used. The hydro-regeneration of the ionic liquid catalyst was performed in a hydrogenation reactor (100) operated at 350° F. (177° C.), 350 psig, 5000 scf $H_2$/bbl ionic liquid catalyst, and 0.2 LHSV in the presence of a hydrogenation catalyst containing Pt and Pd. The hydrogenation reactor effluent [regenerated catalyst effluent (10)] was separated into gas and separated liquid. At these conditions, 80 wt % of the conjunct polymer in the ionic liquid catalyst was converted to a light hydrocarbon material having a boiling point less than 475° F. (246° C.), and the regenerated ionic liquid catalyst contained less than 1% conjunct polymer. The offgas from the gas-liquid separation unit contained mostly $H_2$ and 6000 ppm of HCl.

The regenerated ionic liquid catalyst containing conjunct polymer naphtha, i.e., regenerated ionic liquid catalyst effluent (10), was directly mixed with an effluent from an alkylation reactor (40). In this process scheme, the hydrocarbon in the alkylation reaction effluent, i.e. isobutane, n-butane and alkylate, were acted as a conjunct polymer extraction solvent (55) to extract the conjunct polymer naphtha from the regenerated ionic liquid catalyst. The ionic liquid catalyst and hydrocarbon phase containing the extracted conjunct polymer naphtha and alkylate were separated by the catalyst and hydrocarbon separator (500) that was a coalescer. The coalescer separated an ionic liquid catalyst stream (60) for recycle back to the alkylation reactor (300). The hydrocarbon stream from the catalyst and hydrocarbon separator (500, i.e. coalescer), containing the extracted conjunct polymer naphtha (45) combined with the alkylate products (80) from the alkylation reactor (300), was sent to a distillation column for product separation. The product properties of blended alkylate gasoline (97) produced by the simplified extracted naphtha blending scheme are shown in Table 6.

TABLE 6

Properties of Blended Alkylate Gasoline Containing Conjunct Polymer Naphtha Prepared by Direct Blending

| | ASTM Test No. | Direct Blending of Alkylate Gasoline with Extracted Conjunct Polymer Naphtha [As-Produced Blend, 97] |
|---|---|---|
| IBP, ° F. | D86-11b | 107 |
| 10%, ° F. | | 168 |
| 50%, ° F. | | 209 |
| 90%, ° F. | | 288 |
| Final Boiling Point, ° F. | | 406 |
| Sulfur, ppm | D7039-07 | <2 |
| Washed gum, mg/100 mL | D381-12 | <2 |
| Ag Strip Test | D4814-11b | 0 |
| Cu Strip Test (3 h/50° C.) | D130-10 | 1a |
| Research Octane Number | D2699-11e1 | 91 |
| Motor Octane Number | D2700-11e1 | 89 |
| AKI [(RON + MON)/2] | D4814-11b | 90 |
| Methylcyclohexane Content | D6729 | 140 ppm |

The results in Table 6 showed that alkylate product produced by this simplified process was as good as the blend (97) prepared from separate alkylate (80) and extracted conjunct polymer naphtha (45) shown in Table 3. This simplified process eliminated an extractor, extraction solvent tank, extraction solvent stripper, and extracted conjunct polymer naphtha tank. The simplified, direct blending of extracted conjunct polymer naphtha (45) lowered the cost for the equipment and also improved process reliability.

Example 8

Methylcyclohexane Content of Alkylates from Various Alkylation Processes and Effect of Extracted Conjunct Polymer Naphtha Blending We examined the methylcyclohexane content of alkylate made with different alkylation catalysts and process configurations. Table 7 summarizes the methylcyclohexane content measurements of alkylate samples made by three different alkylation processes.

TABLE 7

Effects of Alkylation Process and Extracted Conjunct Polymer Naphtha Blending on Content of Methylcyclohexane in Final Alkylate Blend

| Alkylation Process | Olefin Feed | Alkylate | Methylcyclohexane Content, ppm |
|---|---|---|---|
| $H_2SO_4$ Process | $C_4^=$ | Alkylate only | <10 |
| HF Process | $C_3^=$ and $C_4^=$ | Alkylate only | 40 |
| Ionic Liquid Process | $C_3^=$ and $C_4^=$ | Alkylate only | 30 |
| Ionic Liquid Process with Direct Blending of Extracted Conjunct Polymer Naphtha (Example 7) | $C_3^=$ and $C_4^=$ | Blend of alkylate and extracted conjunct polymer naphtha | 140 |

Our study found that isobutane alkylation with C3/C4 olefin feed or C4 olefin feed produces only very small amounts of methylcyclohexane (less than 50 ppm), independent of the alkylation catalyst and process. For example, sulfuric acid alkylation process with $C_4$ olefin feeds produced <10 ppm of methylcyclohexane and hydrofluoric acid alkylation process with $C_3$ and $C_4$ olefin feed produced alkylate with 40 ppm of methylcyclohexane. Alkylation process with an ionic liquid catalyst, as reported in Example 2, produced alkylate with 30 ppm of methylcyclohexane.

When the extracted conjunct polymer naphtha was blended directly to the alkylate products (80) the amount of methylcyclohexane in alkylate blend increased to 140 ppm.

This study showed that direct blending of hydrogenated, extracted conjunct polymer naphtha (45) can be detected by the presence of methylcyclohexane or other naphthenic trackable molecules, and the blending level could be estimated. Based on the methylcyclohexane content, we estimated approximately 0.1 vol % of extracted conjunct polymer naphtha (45) was blended to the alkylate products (80) in the final blend of Example 7 via direct blending.

The transitional term "comprising", which is synonymous with "including," "containing," or "characterized by," is inclusive or open-ended and does not exclude additional, un-recited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

It is claimed:

1. An integrated alkylation process, comprising:
   a. regenerating a used ionic liquid catalyst comprising a conjunct polymer in a hydrogenation reactor (100) to make a regenerated catalyst effluent (10);
   b. mixing the regenerated catalyst effluent (10) or a separated liquid from the regenerated catalyst effluent (10) with an effluent from an alkylation reactor (40) to make a mixture; and
   c. separating out an ionic liquid catalyst stream (60) from the mixture made in step b) to produce a blended alkylate gasoline (97) comprising greater than 50 wppm methylcyclohexane.

2. The integrated alkylation process of claim 1, wherein conditions in the hydrogenation reactor (100) are selected to produce a hydrogenated conjunct polymer naphtha having a property selected from a group consisting of a final boiling point less than 246° C. (475° F.), a Bromine Number of 5 or less, at least 30 wt % naphthenes, at least 3 wt % methylcyclohexane, and combinations thereof.

3. The integrated alkylation process of claim 1, wherein conditions in the hydrogenation reactor (100) are selected to produce a hydrogenated conjunct polymer naphtha having a final boiling point less than 246° C. (475° F.), a Bromine Number of 5 or less, and at least 30 wt % naphthenes.

4. The integrated alkylation process of claim 1, wherein the regenerated catalyst effluent (10) or the separated liquid from the regenerated catalyst effluent (10) comprises a hydrogenated conjunct polymer naphtha.

5. The integrated alkylation process of claim 4, wherein the hydrogenated conjunct polymer naphtha has a final boiling point less than 246° C.

6. The integrated alkylation process of claim 4, wherein the hydrogenated conjunct polymer naphtha has a Bromine Number of 5 or less.

7. The integrated alkylation process of claim 4, wherein the hydrogenated conjunct polymer naphtha has at least 30 wt % naphthenes.

8. The integrated alkylation process of claim 4, wherein the hydrogenated conjunct polymer naphtha has a final boiling point less than 246° C., a Bromine Number of 5 or less, and at least 30 wt % naphthenes.

9. The integrated alkylation process of claim 4, wherein the hydrogenated conjunct polymer naphtha has at least 3 wt % methylcyclohexane.

10. The integrated alkylation process of claim 1, wherein the blended alkylate gasoline (97) comprises up to 500 wppm methylcyclohexane.

11. The integrated alkylation process of claim 1, wherein the used ionic liquid catalyst has the formula Q+A−, wherein Q+ is an ammonium, a phosphonium, a boronium, an iodonium, or a sulfonium cation and A− is a negatively charged ion.

* * * * *